United States Patent
Spera et al.

(10) Patent No.: US 9,340,806 B2
(45) Date of Patent: May 17, 2016

(54) METHOD OF INITIATING ACETIC FERMENTATION UNDER INDUSTRIAL CONDITIONS

(71) Applicants: Maria Spera, Mysiadło (PL); Irena Sikorska, Warsaw (PL); Anna Misiewicz, Warsaw (PL)

(72) Inventors: Maria Spera, Mysiadło (PL); Irena Sikorska, Warsaw (PL); Anna Misiewicz, Warsaw (PL)

(73) Assignee: Instytut Biotechnologii Przemyslu Rolno-Spozywczego, Warsaw (PL)

( * ) Notice: Subject to any disclaimer, the term of this patent is extended or adjusted under 35 U.S.C. 154(b) by 0 days.

(21) Appl. No.: 14/388,472

(22) PCT Filed: Mar. 28, 2013

(86) PCT No.: PCT/EP2013/056793
§ 371 (c)(1),
(2) Date: Sep. 26, 2014

(87) PCT Pub. No.: WO2013/144327
PCT Pub. Date: Oct. 3, 2013

(65) Prior Publication Data
US 2015/0111267 A1   Apr. 23, 2015

(30) Foreign Application Priority Data
Mar. 30, 2012   (PL) .......................... 398670

(51) Int. Cl.
*C12J 1/04* (2006.01)
*C12P 7/54* (2006.01)
*C12J 1/02* (2006.01)

(52) U.S. Cl.
CPC .... *C12P 7/54* (2013.01); *C12J 1/02* (2013.01); *C12J 1/04* (2013.01)

(58) Field of Classification Search
None
See application file for complete search history.

(56) References Cited

U.S. PATENT DOCUMENTS

| 2,997,424 | A  | * | 8/1961 | Mayer | ........................... 435/140 |
| 2009/0238919 | A1 | * | 9/2009 | Muroki et al. | .................. 426/17 |
| 2010/0028487 | A1 | * | 2/2010 | Ogasawara | .................... 426/17 |

FOREIGN PATENT DOCUMENTS

| PL | 164743 | B1 | * | 10/1994 |
| SU | 1337406 | A1 | * | 9/1987 |

OTHER PUBLICATIONS

PCT International Publication No. WO 2002/08438 A2 (Bioengineering Resources Inc [US]; Gaddy James [US]; Arora Dinesh K); published Jan. 31, 2002.
Great Britian Patent No. GB 1 101 560 A, (Heinrich Frings G M B H); published Jan. 31, 1968.
International Search Report issued by the International Searching Authority (ISA/O.E.P.M.) on Jul. 12, 2013 in connection with International Application No. PCT/EP2013/056793.

* cited by examiner

*Primary Examiner* — Robert Yamasaki
*Assistant Examiner* — Charles Zoltan Constantine
(74) *Attorney, Agent, or Firm* — Gary J. Cershik; Cooper & Dunham LLP

(57) ABSTRACT

The subject of the present invention is a method of initiating acetic fermentation in a production fermenter using a starter culture cultured in a pilot fermenter which constitutes about 1-3% of the working volume of the production fermenter, and the production fermenter is inoculated in a continuous fashion with acetic fermentation bacteria cultured in the pilot fermenter.

8 Claims, 4 Drawing Sheets

METHOD OF INITIATING ACETIC FERMENTATION UNDER INDUSTRIAL CONDITIONS

Figure 1:
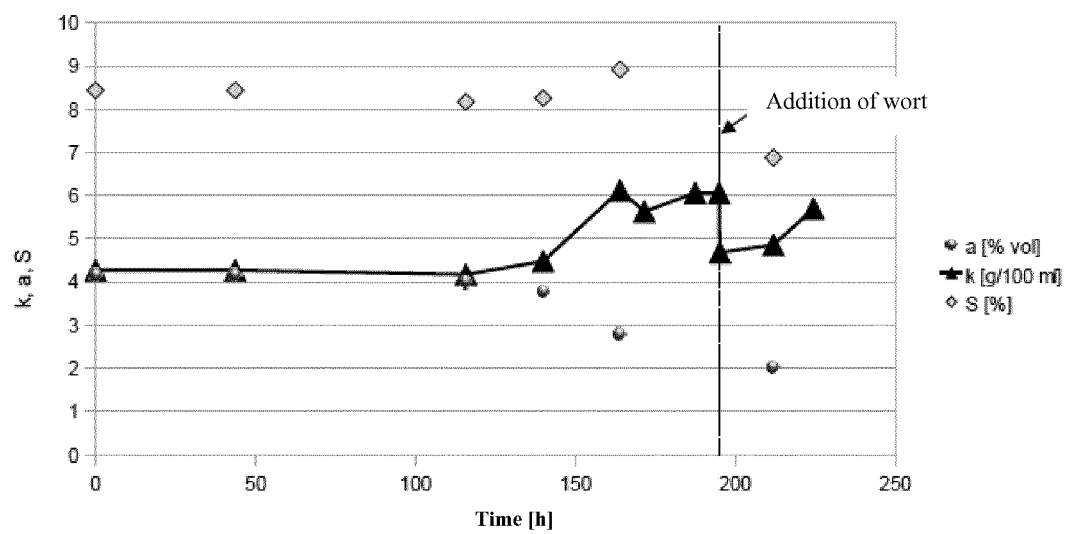

This application is a §371 national stage of PCT International Application No. PCT/EP2013/056793, filed Mar. 28, 2013, designating the United States and claiming priority of Polish Application No. PL398670, filed Mar. 30, 2012, the contents of all of which are hereby incorporated by reference into this application.

The subject of the present invention is a method of initiating acetic fermentation conducted under industrial conditions. The present invention belongs to the area of biotechnological processes used in the food industry.

Acetic acid bacteria are known for their ability to rapidly and incompletely oxidize substrates that are carbon sources, particularly sugars and alcohols. These properties are utilized in many biotechnological processes, in particular in vinegar manufacturing, in which acetic acid is produced from ethanol.

Vinegar is a product obtained through alcohol fermentation, and then acetic fermentation of appropriate sources of plant origin containing carbohydrates, or through the acetic fermentation of products containing ethyl alcohol, obtained from sources of plant origin. Vinegar contains acetic acid at a particular concentration: from 50 g/l to the maximum attainable by biological processes. Vinegar may also contain taste and aroma enhancing additives such as juices and/or juice concentrates, and/or extracts from fruit, vegetables, herbs, spices and other plants and/or plant parts admissible into food.

Cider vinegar (apple) is used as a component of parapharmaceuticals, weight-loss supplements, blood pressure reductants and may be used as a consumer or natural product or as a component of cleaning products.

The production of vinegar makes use of various sources depending on availability and local tradition: Substrates containing ethanol: wine, beer, or fermented fruit juice may be directly subjected to acetic fermentation. Other sources require the preceding fermentation of hydrocarbons to ethanol. Raw materials containing starch must be appropriately prepared prior to alcohol fermentation. The production of vinegar also makes use of diluted spirits from various sources. The best for white vinegar are rectified spirits.

The product obtained through the dilution of acetic acid obtained through chemical synthesis is not vinegar.

Ethyl alcohol is biocatalyzed by appropriate strains of acetic acid bacteria (AAB) to acetic acid. AAB are chemoorganotrophs. They may only use energy released from organic compounds. They are incapable of anaerobic metabolism. Oxygen is always the final electron acceptor. Acetic fermentation is not a fermentation in the strict sense, but a respiration process. The main characteristic of acetic fermentation bacteria is their ability to oxidize ethanol to acetic acid. Presently, acetic acid bacteria are classified into 5 genera: *Acetobacter* (A.), *Gluconacetobacter* (Ga.), *Gluconobacter* (G.), *Acidomonas* (Ac.) and *Asaia* (As.). The present document makes use of the older classification into *Gluconobacter* and *Acerobacter*. The following are indicated among bacteria of industrial utility: *Gluconobacter, Gluconacetobacter* and *Acetobacter*. *Gluconobacter* are obligate aerobes, and oxidize ethanol solely into acetic acid. Sugars degrade as the acid is formed. *Gluconobacter* occur in flowers, fruit, and vegetables South African dairy-based beer, apple wine, wine, wine vinegar, baker's yeast and garden soil. Bacteria of the genera *Gluconacetobacter* and *Acetobacter* oxidize ethanol to acetic acid and further to $CO_2$ and $H_2O$. Acetates and lactose are oxidized to carbon dioxide and water. *Acetobacter* occurs on fruit, vegetables, soured fruit juices, alcoholic beverages and vinegar. *Acetobacter xylinum* are capable of producing cellulose and grow on liquids in the form of a film. In the vinegar industry, particularly in bedded fermentation, because they obstruct the bedding.

Most acetic bacteria species oxidize glucose to gluconic acid or even ketogluconic acid. Some oxidize maltose and saccharose. They can produce oxalic acid from many sugars and organic acids.

Strains of acetic acid bacteria usually grow at temperature from several to 40° C. Most, however, do not tolerate temperature above 37° C. The optimal temperature is dependent on culture conditions: ethanol and acetic acid concentrations, medium component availability, oxygen concentration and is usually in the range 25-30° C.

The optimal medium for the growth of acetic acid is in the range pH 5.0-6.0. The bacteria grow and form acetic acid in media with a pH 4.0-4.5. In neutral or alkaline media these microorganisms grow very slowly. Under industrial conditions, adapted strains of acetic bacteria multiply and produce acetic acid at a pH of 3 and lower.

Oxygen is a substrate of acetic fermentation. Depending on the summary concentration of the fermentation liquid, the methods of conducting the fermentation and it intensity, a minute pause in aeration stop the fermentation and may lead to bacterial mortality.

Both the substrate, ethanol as well as acetic acid are inhibitors of the growth of acetic bacteria. For this reason, bacterial growth is possible only at certain concentration ranges of these substances.

Ethanol concentration during fermentation should not exceed 4-5% vol. Some strains, depending on the medium, may survive an ethanol concentration of 10-16% vol., but the higher alcohol concentration should result in a lower acetic acid concentration. *Acetobacter* and *Gluconacetobacter* are capable of peroxidation. Following the depletion of ethanol they may oxidize acetic acid to $CO_2$ and $H_2O$ (at a summary medium concentration of about 6-7%). This process is very undesirable in industry, and can cause considerable damage.

Acetic fermentation may be conducted in containers with a fill. They grow on the surface of the fill or in submerged fermentation, suspended in liquid.

In the surface methods, the bacteria are cultured on the surface of the liquid in the form of a film and may "crawl" onto the sides of the container. This is the oldest method, and using it a wine or fruit vinegar of 8% may be formed. A certain modification of the surface method is the flow-through method, wherein the gas-liquid phase boundary is developed. In these methods the liquid flows over a porous material, usually beech shavings, and thus the gas-liquid phase boundary. An industrial example of the flow-through method is the generator method, in which fermentation is conducted in a wooden vat equipped with a grate. The space above the grate is filled with shavings on which the bacteria grow. The bedding is periodically wetted with the liquid that gathers under the grate. A blower supplies air into the vat. This method was perfected by Frings in 1932.

In the submerged method, bacterial growth and fermentation are conducted in liquid, in tanks from several liters to several dozen cubic meters. In this method, air is supplied by a self-drawing mixer and is dispersed in the form of fine bubbles. During the fermentation, temperature and air flow are regulated, and alcohol concentration may be measured as well. The installed pumps ensure the automatic filling and emptying of the tank. The submerged fermentation method facilitates the production of vinegar in larger quantities and on a larger scale than surface methods.

Acetic fermentation under industrial conditions may be conducted using a homogenous bacterial culture, cultured from a single initial strain, most often under laboratory conditions or a mixture of strains, obtained during sequential samplings during the fermentation of the so-called mother of vinegar. Mother of vinegar is obtained from a previous fermentation and is often a mixture of "unidentified" strains obtained through the autologous selection of previous acetic fermentations. Mother of vinegar contains unfermented ethanol, usually around 1-2% by volume. Mother of vinegar is stored at a temperature from a dozen to over 20 degrees centigrade, with access to air, but during storage (several to several dozen hours) the liquid volume is not mixed nor aerated, which decreases the number of live cells and changes the composition of the microorganism population. During storage, the acetic acid bacteria largely become inactive due to their high sensitivity to low oxygen.

The presently used methods of initiating acetic fermentation under industrial conditions are dependent on the type of vinegar produced, its strength, the equipment, traditions and access to appropriate microorganisms. In surface methods, including flow-through methods, when the fermentation intensity is lesser and the vinegar produced has a lower acidity, the fermentation inoculation makes use of the so called mother of vinegar. Its use does not guarantee conditions in which fermentation will occur using the most advantageous bacterial strain, all the more so, since the fermentation is not conducted under sterile conditions.

In submerged fermentation vats, from several to several dozen cubic meters in volume or more, acetic fermentation may be initiated using a starter culture from another, most preferably adjacent and active fermentation, or using mother of vinegar from another production unit, or using a most often homogenous starter culture from an active pilot fermenter.

During the initiation of fermentation, it is necessary to appropriately and continuously mix and aerate the fermenting liquid, as well as to regulate the temperature and periodically monitor acidity. The time necessary to initiate the production fermenter, meaning an observed change in acidity demonstrated by common analytical methods, is dependent on the amount, physiological state and source of bacteria used for the inoculation, and may last from several days to as much as several weeks.

Acetic fermentation is conducted using bacterial strains, which may be included among the extrempophiles characterised by their ability to grow and ferment in a low pH environment. In industry, the process occurs under non-sterile conditions. Air is not sterilised, and only larger solid particles may be filtered off. In industry, mainly to limit the loss of ethanol through evaporation which may affect the overall process, the fermentation is conducted in relatively airtight containers.

In fermentative production, following inoculation of the wort with the acetic bacteria starter culture and their subsequent proliferation, the fermentation process may be conducted using one of either periodic or continuous methods.

The known state of the art discloses the periodic inoculation of industrial acetic fermentations, using the periodic method.

The periodic method is divided into charges. A charge lasts from the pouring of the wort to the fermentation of the alcohol to a defined concentration (as low as possible under the available technological conditions, as low as 0.3-0.2% vol.). Towards the end of the charge, a portion of the fermenting liquid is drawn off into production fermenter (usually ½), and fresh wort is added into the fermenter. When producing 10% vinegar, the wort contains about 1 g/100 ml acetic acid, 10% vol. ethanol and an appropriate quantity of medium. The periodic method may be used to obtain various types of vinegar. When producing white vinegar with a concentration of 10 g/100 ml and a 50% exchange of medium volume, charges last about 20-24 hours. When weaker vinegars are made, the charges are shorter. The periodic method may be used to obtain vinegars with a concentration of about 16 g/100 ml (single-stage fermentation, adapted bacterial strain). Attention should be drawn to the fact that the higher the summary concentration in the fermentation, the more dangerous is oxygen starvation. When fermenting a wort with a summary concentration of 11%, and even 15 second interruption in aeration may significantly hinder the fermentation, protract the charge by several hours, and significantly decrease the fermentation rate in the next 3-4 charges.

Furthermore, in a fermentation using the periodic method it is vital not to permit excessive fermentation of ethanol. This entails the mortality of bacteria, the need to regenerate the starter culture, a protraction of the proliferation time of the starter culture, and protracted proliferation times of bacteria in subsequent fermentation cycles. Usually, the time elapsed between the addition of consecutive portions of inoculate is from several to twenty hours and depends on the fermentation rate, or mainly the summary concentration of liquid in the pilot fermenter. The inoculation of an industrial fermentation in this way lasts several days, and the time depends on the summary concentration of the wort.

Publication SU 1337406 discloses a method of culturing bacteria for the production of vinegar in a cascade fermentation, in which acetic acid bacteria collected from a test tube or from the main fermentation cascade are cultured in a starter fermentation with a working volume of about 60-80% of the main fermentation, until an acetic acid concentration is achieved equal to the concentration in the main fermentation, which corresponds to a particular growth phase of the bacteria. At the same time, the entire culture from the main fermentation is transferred to the second fermentation of the cascade, and the main fermentation is loaded with the liquid from the pilot fermenter. This population renewal in the main fermentation is repeated every 20-30 days of continuous culture. The pilot fermenter cultures are conducted cyclically.

Description PL 164743 discloses a method of producing vinegar using *Acetobacter aceti* MW-2 bacteria, in which the initiation of fermentation uses a strain isolated and stored in a stationary surface culture on a semi-liquid medium.

Bacteria proliferated on semi-liquid media are transferred to a fermentation of several liters in volume (working volume of 3 $dm^3$) containing production medium. The contents of this fermentation are inoculated into a production fermenter, in which fermentation is conducted using a known method, meaning that after alcohol is fermented to 0.2-0.5% vol., 20-50% of the fermentation contents are exchanged for fresh wort with an alcohol content of 10-14% by volume and 1-2 g/100 ml acetic acid with continuous aeration. The method of fermentation in the pilot and industrial fermentations is identical.

After fermenting the alcohol to 0.5% by volume, a portion of the liquid is removed from the pilot fermenter, leaving 1.5 $dm^3$ and the same volume of wort is added. The industrial fermenter loaded with aerated and heated wort with the same composition as the pilot fermenter is periodically inoculated with the inoculate from the pilot fermenter. Following several additions of the liquid from the pilot fermenter into the industrial fermentation, an increase in acetic acid concentration was noted. After increase in acetic acid concentration above 0.5 g/100 ml per day was noted, the inoculation process was deemed complete.

The vinegar obtained using the industrial fermentation is then used to initiate fermentation in subsequent industrial fermentations using a known method.

The problem in the state of the art is the lack of an elastic process for conducting an acetic fermentation. In extant technologies, the vinegar production process required constant monitoring of the fermentation process in the pilot fermenter as well as during the inoculation of the production fermenter in order to maintain appropriate conditions and to prevent a decrease in the efficiency of the process. For example, in the periodic method, a transgression of the recommended alcohol concentrations causes a decrease in bacterial activity, which hinders the continuous production and even their mortality. Furthermore, it is necessary to repeat the inoculation process, which prevents continuous production and greatly increases the time necessary for the initiating the production fermenter and, by the same token, production of the final product.

Unexpectedly, the present invention delivers a solution for the above problems.

The subject of the present invention is a method of initiating acetic fermentation in production fermenter using a starter culture cultured in a pilot fermenter, constituting about 1-3% of the working volume of the production fermenter, characterised in that the industrial fermentation is inoculated in a continuous method with acetic fermentation bacteria cultured in the pilot fermenter.

Preferably, the alcohol concentration in the liquid leaving the pilot fermenter is about 0.3 to 3% by volume, and the acetic acid concentration is from 3 to 7 g/100 ml.

Preferably, the degree of aeration of the liquid in the pilot fermenter is 30-80%.

In the next preferable embodiment of the present invention, the summary concentration of the liquid used as the inoculate is from 4 to 10%.

The present invention relates to a method of initiating acetic fermentation in the production fermenter in a volume of several cubic meters or more using a starter culture from a pilot fermenter with a working volume of several to several dozen liters (from 2 to 25 l), which constitutes from 1-3% of the working volume of the industrial fermentation. According to this method, the pilot fermentation is a continuous fermentation. The liquid leaving the pilot fermentation flows directly into the production fermenter, inoculating the contents of the production fermenter. After several dozen hours of the inoculation process, changes in alcohol concentration (decrease) and acetic acid concentration (increase) are observed in the production fermenter, which is indicative of the initiation of fermentation. After the fermentation is initiated in the production fermenter, the production wort is added into the fermentation. It is possible to wait until alcohol is fermented off to a predetermined concentration, or wort may be added immediately. The wort may be added continuously, with a constant or varying rate of flow, or in one or several portions. After a certain period from the onset of inoculation, the number of bacteria in the industrial fermentation grows due to proliferation and is sufficient to conduct a periodic or continuous fermentation. After the initiation of fermentation it is also possible to increase the summary concentration of the fermentation liquid through the addition of a wort with higher summary concentration and to produce a stronger vinegar (acetic acid concentration of as much as 12.5-13 g/100 ml).

This method is used in the production of cider vinegar, but it may also be used to initiate fermentation using any substrate.

In the pilot fermenter, where fermentation is conducted using a constant method, the summary concentration of the liquid in the fermenter, encompassing the acetic acid concentration and ethanol concentration and the wort resupplying the fermentation may be from several to 10%. In the pilot fermenter, the ethyl alcohol is not fermented off completely, which means that its concentration in the liquid leaving the fermentation is 0.3-3% vol.

In the production fermenter, the wort produced has a volume adapted to the technical conditions (i.e. a level that covers the mixer turbine, a level that ensures the appropriate aeration, a level ensuring heat exchange between the fermentation liquid and radiator and thereby liquid heating or cooling). This is usually a volume of several $m^3$, less than half the working volume of the fermenter. The summary concentration of the wort is 4-10%. The wort is heated to a temperature, in which fermentation is conducted (25-35° C.), depending on the summary concentration of the liquid in the fermenter. The wort is mixed and aerated continuously. The worts used for the pilot and production fermentations may have different summary concentrations and compositions. The wort used, both that to supply the pilot as well as the production fermenters may contain alcohol from any source (wine) or from rectified spirit, and in addition to the alcohol may contain acetic acid obtained from fermentation. The summary concentration of the dosed wort may be from 4.0 to 10% in the case of continuous fermentation or from 6.0 to 13.5% in the case of initiating a production fermentation with the intent to conduct periodic fermentation. The proportions between ethanol and acetic acid in the wort are from 10:1 to 5:1.5. Depending on the source and composition of the raw material used in it, the wort may be enriched with the addition of appropriate ingredients that are nitrogen and carbon sources, a mineral addition as well as biostimulants, should these be absent or present in insufficient concentrations in the material used.

The dilution rate used in the pilot fermenter must be selected so as not to cause bacteria to be washed out of the fermentation. The dilution rate depends on the summary concentration of the liquid in the fermenter, the summary concentration of the dosed wort, the composition of wort, the temperature of fermentation and the rate of aeration. The advantage of the present invention is a decreased time of initiation of the production fermentation with comparison to known methods as well as no need to continually monitor the course of the fermentation in the pilot fermenter during the inoculation of the industrial fermentation. After setting the conditions of the pilot fermentation, the inoculation process of the production fermenter may be conducted continuously and over an arbitrary period of time when maintaining the resupply of wort to the pilot fermenter, the maintenance of the appropriate aeration as well as temperature. A process embodied according to the present invention is elastic because it permits the optimization of preferable ethanol concentration ranges in the liquid leaving the pilot fermenter (0.3-3%) due to the biomass product. The use of an insufficient rate of dilution even for several to several dozen hours does not cause mortality among the microorganisms. Whereas the use of an excessive dilution rate will not cause an immediate washout of microorganisms from the pilot fermenter. In turn, the inoculation procedure need not be repeated, the inoculation may be constant and overfermentation is not a danger.

During the fermentation of wine and grain vinegars, due to the properties of the raw material, the low surface tension of the wort as well as the presence of "foamants" much foam is formed. For example, much foam is formed during the fermentation of cider wort, during the mixing of the liquid in the fermenter and the pumping of cider wort. In the periodic method, the foam forms only during a particular period (over 0.5-1.0 h), but there are large quantities thereof and it causes unfermented product to effervesce from the fermentation. The continuous process according to the present invention significantly reduces the degree of foaming.

FIG. 1 Initiation of acetic fermentation using the $O_4$ strain in a laboratory fermenter.

Figure 2:
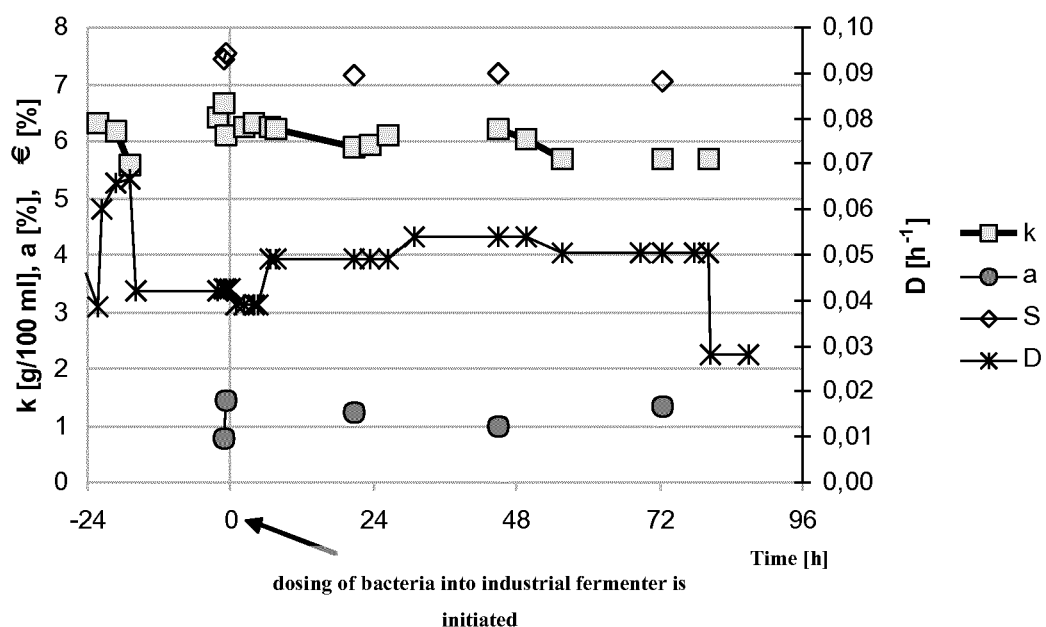

FIG. 2 The course of fermentation in a pilot fermenter a day prior to initiating the inoculation of an industrial fermentation until the termination of the inoculation of the industrial fermentation. The inoculation of the industrial fermentation was initiated at the point marked "0" on the time axis.

Figure 3:
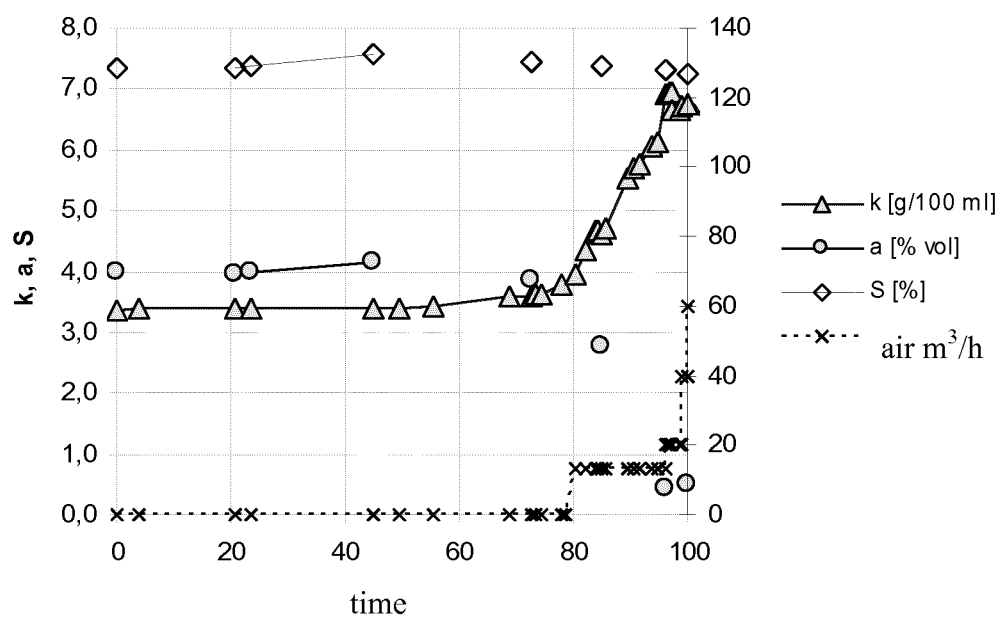

FIG. 3 The course of fermentation in the industrial fermentation during the inoculation with bacteria from the pilot fermenter.

Figure 4:
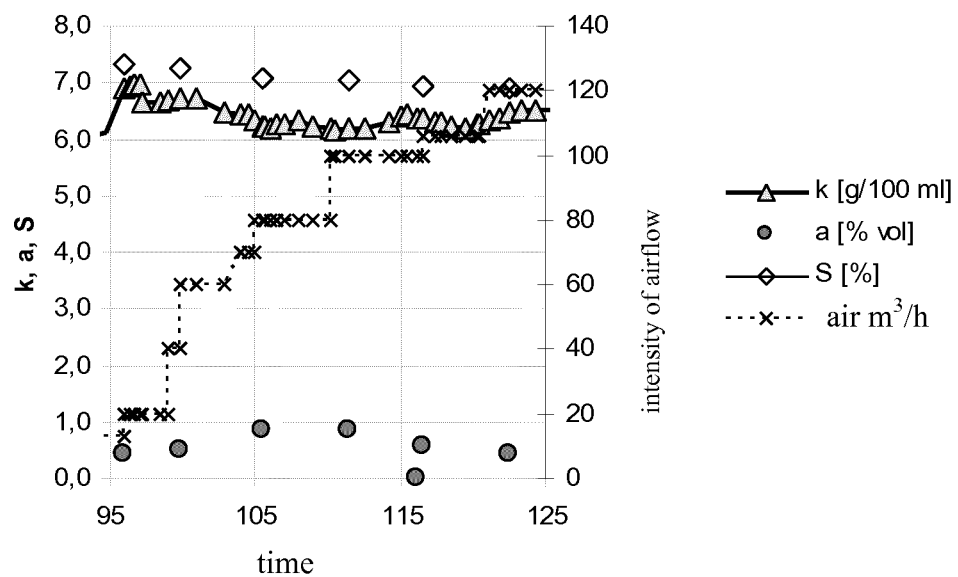

FIG. 4 The course of continuous fermentation during industrial fermentation.

The nature of the present invention is described in detail in the example embodiment.

EXAMPLE

The proliferation of bacteria from a slant was performed in a microtechnical (laboratory) fermenter with a working volume of 3 liters. The fermenter was inoculated one time with the $O_4$ strain of *Acetobacter pasteurianus*, registered in the Kolekcja Kultur Drobnoustrojów Przemysłowych (IBPRS) under the accession number KKP 674. This strain is characterised by the highest technical parameters during culturing on a shaker. Acetic acid bacteria are cultured on a medium denoted with the symbol SS(1+3). This is a solid medium with an acid content of about 1 g/100 ml (as acetic acid) and containing about 3% vol. ethanol. Following inoculation, the slants were thermostabilised in a heater at a temperature 28-30° C. for 4-5 days. After this time, the cultured bacterial biomass was used to inoculate subsequent slants. The bacterial biomass from one slant was used to inoculate 5-6 subsequent slants.

Next, the starter wort was inoculated in the microtechnical fermenter with bacterial biomass from agar slants at a dose of biomass from one slant per 100 ml wort. The fermenter was filled to half its working volume with pasteurized starter wort, which was the liquid medium CC(3+4) (a mixture of cider, chemically unfixed cider vinegar and water in such proportions so as to achieve an acid content of the medium of about 3 g/100 ml (as acetic acid), and an alcohol content of about 4% vol. The wort was enriched by enriching the composition of the medium with: glucose—1 g/l and diammonium phosphate—0.45 g/l). The wort was heated to a temperature of 30° C. The mixer was turned on, and the air regulator valve was closed until the rate of change of acid content was 0.1 g/100 ml per day, and then the air supply was regulated taking into account a reserve for the predicted increase in requirements. After the alcohol is fermented down to a concentration of 1% vol., the fermentation was resupplied with production cider wort CC(1+6) to the full working volume. The production cider wort was the CC(1+6) medium obtained through the acidification of cider with cider vinegar and dilution with water, so as to obtain the required acid and alcohol concentration. The wort was enriched with glucose at a dose of 1 g/l and diammonium phosphate at a dose of 0.45 g/l.

FIG. 1 shows changes in the acidity (k), alcohol concentration (a—analyzed value) during the proliferation of $O_4$ strain bacteria in the microtechnical fermenter. The graph also indicates changes in the summary concentration Σ (S) of the liquid in the fermenter obtained using analyses and calculations (Σ=k+a).

After several dozen (70-90) hours from inoculation, we observed a decrease in the oxygen saturation of the wort, a sign of its depletion by the bacteria. After 3-4 days, the degree of the oxygen saturation of the wort decreased to under 20 percent, which entails a significant limitation of the rate of fermentation by oxygen starvation. During this time, the rate of acidity increase was about 0.004 g/(l·h). From this moment, we opened the air supply valve and adjusted the mixer revolution controller depending on the forming oxygenation level in the wort so as to prevent the oxygen saturation in the wort from falling below 50%. As the acidity increased, we resupplied the fermentation with lots of production cider wort, medium CC(1+6), until we attained a volume of 2.5 liters. Next, taking into account the unitary production and volume of the liquid in the fermenter, we initiated a constant production wort resupply at an initial rate of 0.03 $h^{-1}$, correcting it in accordance with the observed changes in acidity. After attaining the desired volume of liquid in the fermenter, 2.5 liters, we continued the constant wort inflow and initiated the outflow of vinegar from the fermentation, so as to maintain a constant liquid level in the fermenter, and the residual alcohol level maintained at 0.3-0.5% vol. Airflow was regulated according to the indications from the oxygen electrode. Prior to transferring bacteria from the laboratory fermenter to the pilot fermenter, we increased the rate of dilution so that the ethanol concentration in the fermenter increased to 1% vol.

Next, the contents of the microtechnical fermenter were transferred into the activated pilot fermenter and we conducted a continuous fermentation.

Under industrial conditions, we used wort obtained from cider wine acidified with cider vinegar.

We prepared two types of wort: starter and production. Each of the worts was supplemented with a basal medium: 1 g/l glucose as well as 0.45 g/l diammonium phosphate.

In order to initiate acetic fermentation, in the production fermenter we prepared 3 000 l of a mixture containing alcohol at 3.98% vol. and acetic acid at 3.36 g/100 ml. This mixture was composed of cider wort, white vinegar and water. After bringing the temperature to 30° C. and initiating the turbine aeration, the fermenter contents were inoculated with *Acetobacter pasteurianus* KKP 674 bacteria from the pilot fermenter.

The pilot fermenter was placed on a specially prepared platform in the are of the upper lid of the production fermenter.

After the production fermenter was prepared for the initiation, we began the inoculation of the production fermenter with bacteria from the pilot fermenter.

We used continuous inoculation. So as to prevent the excessive fermentation of alcohol, we selected a rate of dilution such that the alcohol concentration in the "mother of vinegar" exiting the pilot fermenter was around 1% by volume.

FIGS. 2 and 3 present changes in acidity (k) and alcohol concentrations (a), as well as the summary concentration of the liquid in the fermenter Σ (S) during the inoculation of the production fermenter.

After 70 h from the initiation of the inoculation, we observed changes in the concentration of acetic acid in the production fermenter. The inoculation of the production fermenter was terminated after 96 hours. In total, the 3000 l of liquid in the production fermenter was inoculated with 20 liters of the liquid containing KKP 674 bacteria from the pilot fermenter.

When an acetic acid concentration of 6 g/100 ml was attained, we initiated the constant supply of wort. We used a continuous, single stage acetic fermentation in the industrial fermenter with submerged use of wort with a summary concentration of 7.1% with an addition of the basal medium dose.

The wort inflow rate was regulated in accordance with the acidity of the liquid in the fermenter, and then depending on the acidity of the vinegar flowing out in the form of fermentation foam, with the intent of maintaining a concentration above 6 g/100 ml and the maximum possible fermentation of ethanol.

The invention claimed is:

1. A method of initiating acetic fermentation in a production fermenter comprising the steps:
    a) culturing a starter culture in a pilot fermenter, wherein said pilot fermenter has a volume of about 1-3% of the working volume of the production fermenter, and wherein said starter culture is a liquid that contains an acetic acid fermentation bacteria, a concentration of ethanol, and a concentration of acetic acid;
    b) continuously transferring the starter culture from the pilot fermenter to the production fermenter and wherein the production fermenter contains a fluid comprising acetic acid, water, and ethanol, whereby the continuous transfer of the starter culture to the production fermenter continuously inoculates the fluid contained within the production fermenter with acetic fermentation bacteria, such that acetic fermentation initiates within the fluid in the production fermenter.

2. The method according to claim 1, wherein the alcohol concentration of the starter culture that is continuously transferred from the pilot fermenter to the production fermenter is from 0.3 to 3% by volume, and the acetic acid concentration of said starter culture is from 3 to 7 g/100 ml.

3. The method according to claim 2, wherein the starter culture in the pilot fermenter is aerated to a degree such that the starter culture has a dissolved oxygen saturation level of 30-80%.

4. The method according to claim 3, wherein the starter culture that is continuously transferred from the pilot fermenter to the production fermenter comprises a summary concentration, whereby the summary concentration is the percent concentration of the acetic acid in the starter culture plus the percent concentration of ethanol in the starter culture, and wherein the summary concentration is from 4 to 10%.

5. The method according to claim 2, wherein the starter culture that is continuously transferred from the pilot fermenter to the production fermenter comprises a summary concentration, whereby the summary concentration is the percent concentration of the acetic acid in the starter culture plus the percent concentration of ethanol in the starter culture, and wherein the summary concentration is from 4 to 10%.

6. The method according to claim 1, wherein the starter culture in the pilot fermenter is aerated to a degree such that the starter culture has a dissolved oxygen saturation level of 30-80%.

7. The method according to claim 6, wherein the starter culture continuously transferred from the pilot fermenter to the production fermenter comprises a summary concentration, whereby the summary concentration is the percent concentration of the acetic acid in the starter culture plus the percent concentration of ethanol in the starter culture, and wherein the summary concentration is from 4 to 10%.

8. The method according to claim 1, wherein the starter culture that is continuously transferred from the pilot fermenter to the production fermenter comprises a summary concentration, whereby the summary concentration is the percent concentration of acetic acid in the starter culture plus the percent concentration of ethanol in the starter culture, and wherein the summary concentration is from 4 to 10%.

* * * * *